United States Patent [19]

Sinofsky

[11] Patent Number: 4,950,266

[45] Date of Patent: Aug. 21, 1990

[54] INFRARED LASER CATHETER SYSTEM

[75] Inventor: Edward L. Sinofsky, Reading, Mass.

[73] Assignee: C. R. Bard, Inc., Murray Hill, N.J.

[21] Appl. No.: 257,760

[22] Filed: Oct. 14, 1988

Related U.S. Application Data

[63] Continuation of Ser. No. 14,990, Feb. 17, 1987, abandoned, which is a continuation of Ser. No. 761,188, Jul. 3, 1985, abandoned.

[51] Int. Cl.$^5$ ............................................. A61N 5/06
[52] U.S. Cl. ........................................... 606/2; 606/7; 606/15; 128/398
[58] Field of Search ............ 128/303.1, 362, 395–398; 372/40, 41; 606/2, 7, 10, 13–16

[56] References Cited

U.S. PATENT DOCUMENTS

| | | | |
|---|---|---|---|
| 1,751,584 | 3/1930 | Hansell | 128/398 |
| 3,327,712 | 6/1967 | Kaufman | 128/398 |
| 3,533,707 | 10/1970 | Weiss | 128/303.1 |
| 3,769,963 | 11/1973 | Goldman et al. | 128/395 |
| 3,884,236 | 5/1975 | Krasnov | 128/303.1 |
| 3,947,780 | 3/1976 | Rice et al. | 372/22 |
| 3,983,511 | 9/1976 | Fricke | 372/67 |
| 4,110,702 | 8/1978 | Chicklis | 372/41 |
| 4,141,362 | 2/1979 | Wurster . | |
| 4,146,019 | 3/1979 | Bass et al. | 128/395 |
| 4,207,874 | 6/1980 | Choy | 128/303.1 |
| 4,233,493 | 11/1980 | Nath | 128/303.1 |
| 4,266,548 | 5/1981 | Davi . | |
| 4,321,559 | 3/1982 | Esterowitz et al. . | |
| 4,330,763 | 5/1982 | Esterowitz et al. | 372/41 |
| 4,350,150 | 9/1982 | Kubota et al. | 128/6 |
| 4,355,893 | 10/1982 | Chicklis | 372/41 |
| 4,383,729 | 5/1983 | Suzuki | 350/96.10 |
| 4,386,428 | 5/1983 | Baer | 372/41 |
| 4,402,311 | 9/1983 | Hattori . | |
| 4,418,688 | 12/1983 | Loeb | 128/303.1 |
| 4,425,503 | 1/1984 | Watkins et al. | 250/345 |
| 4,445,418 | 5/1984 | Modone et al. | 65/3.12 |
| 4,454,882 | 6/1984 | Takano | 128/395 |
| 4,458,683 | 7/1984 | Saito | 128/395 |
| 4,470,407 | 9/1984 | Hussein | 128/303.1 |
| 4,503,854 | 5/1985 | Jako | 128/345 |
| 4,504,297 | 3/1985 | Kosinski et al. | 65/3.12 |
| 4,515,612 | 5/1985 | Burrus, Jr. et al. | 65/3.12 |

(List continued on next page.)

FOREIGN PATENT DOCUMENTS

| | | |
|---|---|---|
| 152766 | 1/1985 | European Pat. Off. . |
| 0153847 | 2/1985 | European Pat. Off. . |
| 144764 | 6/1985 | European Pat. Off. ......... 128/303.1 |
| 178464 | 9/1985 | European Pat. Off. . |
| WO8404879 | 12/1984 | PCT Int'l Appl. . |
| WO8606642 | 11/1986 | PCT Int'l Appl. . |
| 2017506 | 3/1979 | United Kingdom . |
| 8301311 | 4/1983 | World Int. Prop. O. ....... 128/303.1 |
| 1893 | 6/1983 | World Int. Prop. O. ....... 128/303.1 |
| 8301893 | 6/1983 | World Int. Prop. O. ....... 128/303.1 |

OTHER PUBLICATIONS

"Linbectomies, Keratectomies . . . Carbon Dioxide Laser", by Beckman et al; Am. J. Ophthal., vol. 71, No. 6, Jun. 1971, pp. 1277–1283.

(List continued on next page.)

*Primary Examiner*—Lee S. Cohen
*Assistant Examiner*—David Shay
*Attorney, Agent, or Firm*—Wolf, Greenfield & Sacks

[57] ABSTRACT

Laser energy produced by a laser operating in the mid-infrared region (approximately 2 micrometers) is delivered by an optical fiber in a catheter to a surgical site for biological tissue removal and repair. Disclosed laser sources which have an output wavelength in this region include: Holmium-doped Yttrium Aluminum Garnet (Ho:YAG), Holmium-doped Yttrium Lithium Fluoride (Ho:YLF), Erbium-doped YAG, Erbium-doped YLF and Thulium-doped YAG. For tissue removal, the lasers are operated with relatively long pulses at energy levels of approximately 1 joule per pulse. For tissue repair, the lasers are operated in a continuous wave mode at low power. Laser output energy is applied to a silica-based optical fiber which has been specially purified to reduce the hydroxyl-ion concentration to a low level. The catheter may be comprised of a single optical fiber or a plurality of optical fibers arranged to give overlapping output patterns for large area coverage.

41 Claims, 8 Drawing Sheets

U.S. PATENT DOCUMENTS

| | | |
|---|---|---|
| 4,538,608 | 9/1985 | L'Esperance, Jr. et al. .... 128/303.1 |
| 4,556,057 | 12/1985 | Hiruma et al. . |
| 4,559,942 | 12/1985 | Eisenberg .......................... 128/303.1 |
| 4,566,453 | 1/1986 | Kumano et al. ................. 128/303.1 |
| 4,566,765 | 1/1986 | Miyauchi et al. . |
| 4,572,189 | 2/1986 | Smith et al. . |
| 4,576,177 | 3/1986 | Webster, Jr. ...................... 128/303.1 |
| 4,648,892 | 3/1987 | Kittrell et al. .................... 128/303.1 |
| 4,672,969 | 6/1987 | Dew . |
| 4,685,458 | 8/1987 | Leckrone .......................... 128/303.1 |
| 4,750,486 | 6/1988 | Butler et al. . |
| 4,775,361 | 10/1988 | Jacques et al. . |

OTHER PUBLICATIONS

"Current . . . in the Treatment of Atherosclerotic Disease", by Lee et al; Chest, vol. 85, #3, Mar. 1984, pp. 429-434.

"Laser Recannalization of a Atheromatous Vessels Using Fiber Optics", by Ward, Lasers in Surg. & Med., vol. 4, 1984, pp. 353-363.

"Limitations . . . Cautious Approach Warranted", by Lee; Am. J. Cardiol., vol. 56, Jul. 1, 1985, pp. 181-185.

"Fibre Bundle Scanner for Laser Photocoagulation Treatment", by H. Fuji et al; Optics & Laser Technology, Feb. 82, pp. 39-40.

"Selective Photothermolysis: Precise Microsurgery by Selective Absorption of Pulsed Radiation", by Anderson et al; Science, vol. 220, Apr. 1983, pp. 524-527

E. Sinofsky et al., "Calculated Temperature Distribution in Cylindrical Tissue Volume Under Laser Irradiation Below the Vaporization Threshold", Lasers in Medicine; *Proceedings of the S.P.I.E.*, vol. 712, 1987, p. 78.

E. Sinofsky et al., "Measurement of Argon Laser Beam Spreading Through Arterial Plaque", Lasers in the Life Sciences, vol. 1, No. 2, 1988, pp. 143-150.

P. E. McGuff et al., "Studies of the Surgical Applications of Laser Light (Laser Amplification by Simulated Emission of Radiation)", *Surgical Forum*, vol. 14, 1963, pp. 143-145.

Leon Goldman et al., *The Biomedical Laser: Technology and Clinical Applications* (1981).

E. Sinofsky, "Comparative Thermal Modeling of ER-:YAG, HO:YAG, CO2 Laser Pulses for Tissue Vaporization", *Lasers in Medicine: Proceedings of the S.P.I.E.*, vol. 712, 1987, p. 188.

L. Decklebaum et al., "Reduction of Laser-Induced Pathological Tissue Injury Using Post-Energy Delivery", *American Journal of Cardiology*, vol. 56, Oct. 1985, pp. 662-667.

M. Motamedi et al., "Interaction of Laser Radiation with Plaque and a Vessel Wall", ICALEO 1984; Laser Institute of America Technical Digest.

L. Esterowitz et al., "Angioplasty with a Laser and Fiber Optics at 2.9 uM", *S.P.I.E. Conference Notes*, Jan. 1986, Los Angeles, Calif.

"The Happy Merger of Fiber Optics and Lasers", David N. Kay, Information Retrieval No. 22; News RT 167 Electronic Design, vol. 17, 06/21/69.

Solid-State Laser Engineering; Springer-Verlage, New York, Heidelberg, Berlin, 1976; Walter Koechner.

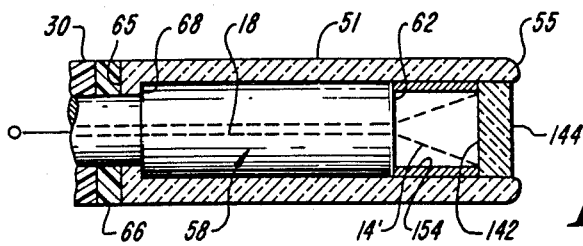
FIG. 6
FIG. 7
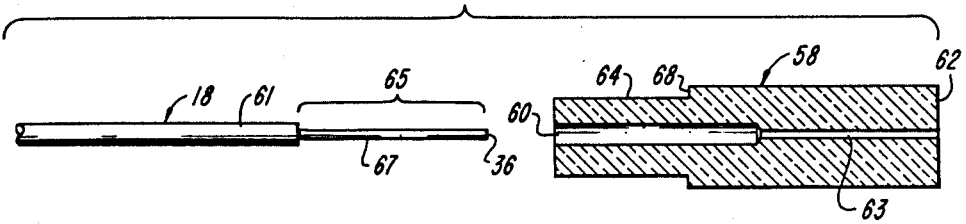
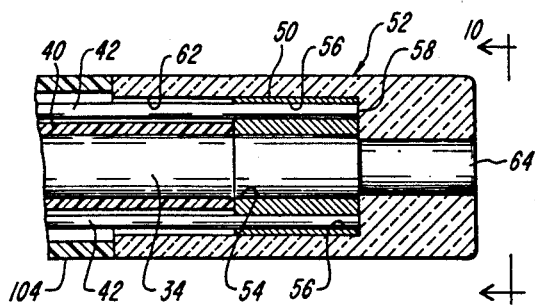
FIG. 9
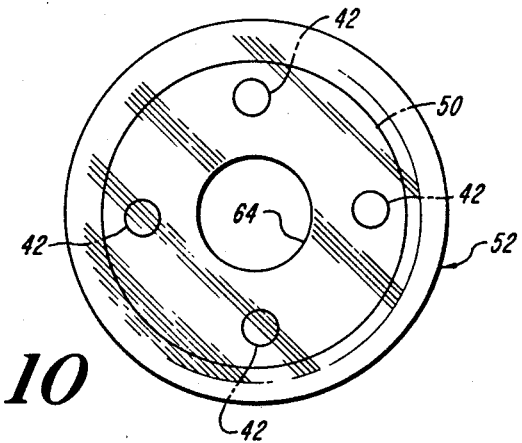
FIG. 10

INFRARED LASER CATHETER SYSTEM

This application is a continuation of application Ser. No. 014,990, filed Feb. 17, 1987, now abandoned, which is a continuation of application Ser. No. 761,188, filed on 07/31185, now abandoned.

FIELD OF THE INVENTION

This invention relates to laser catheters and optical fiber systems for generating and transmitting energy to a surgical site in a living body for the purposes of tissue removal or repair.

BACKGROUND OF THE INVENTION

While lasers have been used for many years for industrial purposes such as drilling and cutting materials, it is only recently that surgeons have begin to use lasers for surgical operations on living tissue. To this end, laser energy has been used to repair retinal tissue and to cauterize blood vessels in the stomach and colon.

In many surgical situations, it is desirable to transmit laser energy down an optical fiber to the surgical location. If this can be done, the optical fiber can be included in a catheter which can be inserted into the body through a small opening, thus reducing the surgical trauma associated with the operation. In addition, the catheter can often be maneuvered to surgical sites which are so restricted that conventional scalpel surgery is difficult, if not impossible. For example, laser energy can be used to remove atherosclerotic plaque from the walls of the vasculature and to repair defects in small-diameter artery walls.

A problem has been encountered with laser surgery in that prior art lasers which have been used for industrial purposes often have characteristics which are not well suited to percutaneous laser surgery For example, a laser which is conventionally used for scientific purposes is an excimer laser which is a gas laser that operates with a gas mixture such as Argon-Fluorine, Krypton-Fluorine or Xenon-Fluorine. Another common industrial laser is the carbon dioxide or $CO_2$ laser.

Both the excimer laser and the $CO_2$ laser have been used for surgical purposes with varying results. One problem with excimer lasers is that they produce output energy having a wavelength in the range 0.2-0.5 micrometers. Blood hemoglobin and proteins have a relatively high absorption of energy in this wavelength range and, thus, the output beam of an excimer laser has a very short absorption length in these materials (the absorption length is the distance in the materials over which the laser beam can travel before most of the energy is absorbed) Consequently, the surgical site in which these lasers are to be used must be cleared of blood prior to the operation, otherwise most of the laser energy will be absorbed by intervening blood before it reaches the surgical area While the removal of blood is possible if surgery is performed on an open area it is often difficult if surgery is to be performed via a catheter located in an artery or vein.

An additional problem with excimer lasers is that the output energy pulse developed by the laser is very short, typically about ten nanoseconds. In order to develop reasonable average power, pulses with extremely high peak power must be used. When an attempt is made to channel such a high peak power output into an optical fiber, the high peak power destroys the fiber. Thus, excimer lasers have a practical power limit which is relatively low. Consequently, when these lasers are used for biological tissue removal, the operation is slow and time consuming.

The $CO_2$ laser has other drawbacks. This laser generates output energy with a wavelength on the order of 10 micrometers. At this wavelength, the absorption of blood hemoglobin is negligible but the absorption by water and tissue is relatively high. Scattering at this wavelength is also very low. Although the $CO_2$ laser possesses favorable characteristics for surgical applications in that it has low scattering and high absorption in tissue, it suffers from the same drawback as excimer lasers in that the absorption length is relatively short due to the high absorption of the laser energy in water. Thus, the surgical area must be cleared of blood prior to the operation.

Unfortunately, the $CO_2$ laser also suffers from a serious additional problem. Due to the long wavelength, the output energy from the carbon dioxide laser cannot be presently transmitted down any optical fibers which are suitable for use in percutaneous surgery (present fibers which can transmit energy from a $CO_2$ laser are either composed of toxic materials, are soluble in water or are not readily bendable, or possess a combination of the previous problems) and, thus, the laser is only suitable for operations in which the laser energy can be either applied directly to the surgical area or applied by means of an optical system comprised of prisms or mirrors.

Accordingly, it is an object of the present invention to provide a laser catheter system which uses laser energy of a wavelength that is strongly absorbed in water, in bodily tissues and atherosclerotic plaque.

It is another object of the present invention to provide a laser catheter system which is capable of providing laser energy that can be transmitted through existing silica-based optical fibers.

It is a further object of the present invention to provide a laser catheter system in which optical scattering is minimized and which has a medium-length absorption length to confine the energy to the area of interest.

It is yet another object of the present invention to provide an optical catheter system with a laser that can be operated on either a pulsed mode or a continuous wave mode.

It is still another object of the present invention to provide a laser catheter system which can be used for biological material removal and biological material repair.

SUMMARY OF THE INVENTION

The foregoing objects are achieved and the foregoing problems are solved in one illustrative embodiment of the invention in which a laser catheter system employs a laser source operating in the wavelength region of 1.4-2.2 micrometers. Illustrative laser sources operating this region are Holmium-doped YAG, Holmium-doped YLF, Erbium-doped YAG, Erbium-doped YLF and Thulium-doped YAG lasers.

In the inventive laser system, the above-noted lasers are used with a specially-treated silica fiber that has been purified to reduce the concentration of hydroxyl (OH-) ions For biological tissue removal, the laser source may be operated in a pulsed mode with a relatively long pulse of approximately 0.2-5 milliseconds at an energy level of approximately 1-2 joules per pulse. With this time duration and energy level, the peak power of the laser pulse is approximately 1 kilowatt. This amount of power can easily be tolerated by the silica fiber, but is sufficient for rapid material removal. With a repetition rate in the range of 1–10 hertz, the average power delivered to a surgical site by such a laser will be under 10 watts.

Alternatively, for biological tissue repair, the laser source can be operated in a low power continuous wave mode to repair, by coagulation, of tissue by a process similar to "spot welding".

BRIEF DESCRIPTION OF THE DRAWING

FIG. 6 of the drawing is an enlarged cross-section of the probe tip the single fiber catheter shown in FIG. 5.

FIG. 7 is an exploded view of a portion of the enlarged cross-section of the probe tip shown in FIG. 6.

FIG. 9 of the drawing is an enlarged cross-sectional view of the probe tip of the catheter shown in FIG. 8 showing the four optical fibers.

FIG. 10 is an end view of the probe tip of the catheter in the direction 10—10 of FIG. 9.

DETAILED DESCRIPTION OF THE PREFERRED EMBODIMENT

Figure 1:
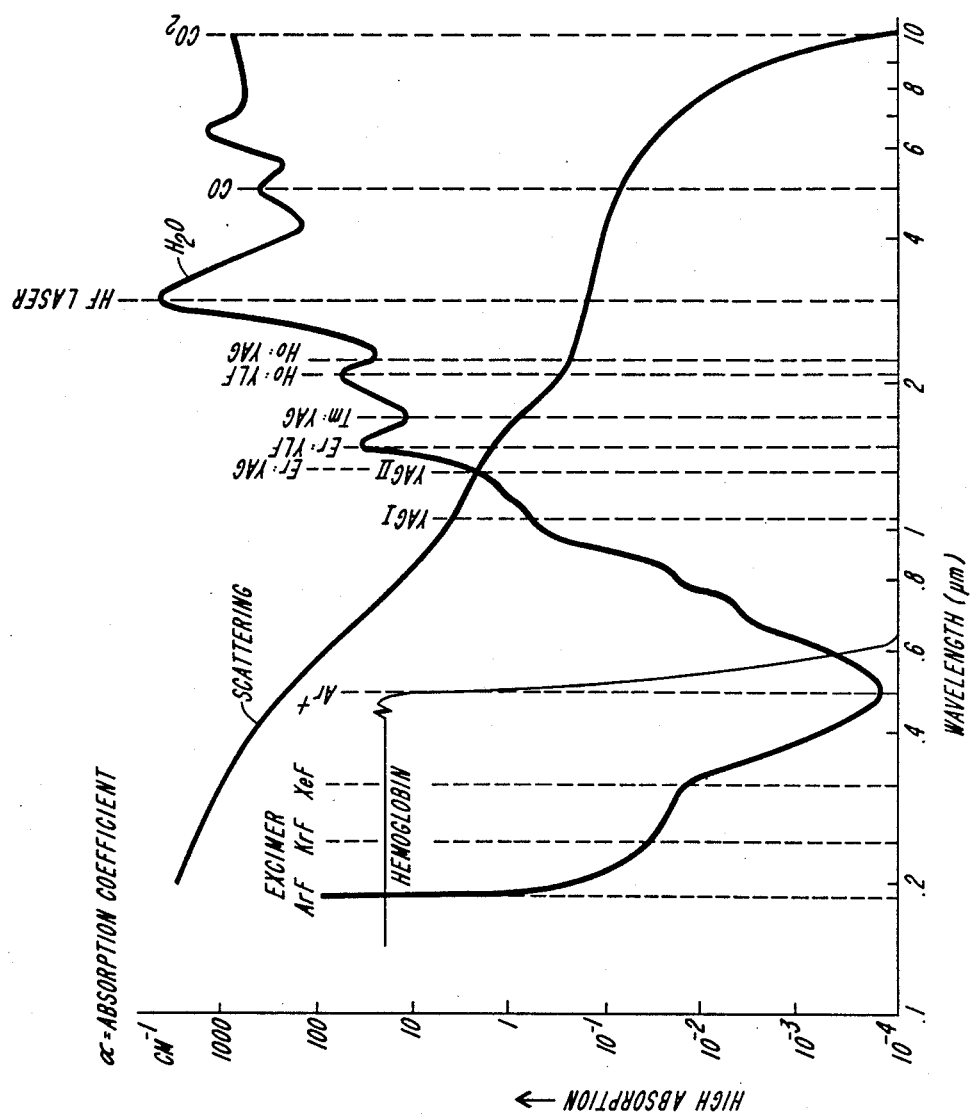
FIG. 1 shows a sketch of absorption of electromagnetic energy versus wavelength and electromagnetic energy scattering versus wavelength.

The absorption and scattering characteristics versus output wavelength of a plurality of known laser systems are shown in FIG. 1. FIG. 1 has a logarithmic scale representing the absorption coefficient in units of $cm^{-1}$ along the vertical axis and the incident energy wavelength in micrometers along the horizontal axis.

From FIG. 1, it can be seen that excimer laser systems which utilize conventional gas mixtures, such as Argon-Fluorine, Krypton-Fluorine and Xenon-Fluorine, and Argon gas lasers produce output energy which falls in the 0.2–0.5 micrometer wavelength region. In this region, the absorption of blood hemoglobin and proteins is very high. Consequently, the absorption length is very short (about 5–10 microns) and virtually no blood can be present between the fiber end and the surgical site during the operation. Thus, it is necessary to remove blood from the surgical area when these lasers are used for surgical purposes.

In addition, for lasers such as Argon, the absorption of water reaches a minimum at 0.5 micrometers so that it is necessary to use a higher power laser than is desirable to achieve sufficient power in the surgical area for material cutting and removal. Also, due to the low absorption of the laser output in water and hemoglobin, the absorption length is very long (approximately 1 mm). In addition, scattering for these lasers is relatively high, causing difficulty in controlling the laser energy and a danger of tissue damage outside the surgical area due to scattering of the laser energy.

At the other end of the wavelength spectrum shown in FIG. 1 are carbon monoxide and carbon dioxide lasers producing outputs at 5 and 10 micrometers, respectively. At these wavelengths scattering is negligible and absorption by water and tissue is relatively high and thus both lasers have good surgical properties. Unfortunately, due to the high absorption of water, the absorption length is relatively short (about 20 microns). Further, silica-based optical fibers in present use which are suitable for percutaneous surgical use have a practical "cutoff" in transmission which occurs approximately at 2.3 micrometers, and, thus, the output energy from carbon monoxide and carbon dioxide lasers cannot be transmitted through such an optical fiber.

In accordance with the invention, laser sources of interest are those that lie in the wavelength range of approximately 1.4–2.15 micrometers. As shown in FIG. 1, in this range, the energy absorption of water is relatively high whereas optical scattering is relatively low. Illustrative lasers which are useful with the present invention comprise Erbium-doped Yttrium Aluminum Garnet (YAG) with a wavelength of 1.55 micrometers, Erbium-doped Yttrium Lithium Fluoride (YLF) with a wavelength of 1.73 micrometers, Thulium-doped YAG with a wavelength of 1.88 micrometers, Holmium YLF with a wavelength of 2.06 micrometers and Holmium YAG at a wavelength of 2.1 micrometers. The absorption of the laser energy produced by lasers in this latter group by water is moderately high and, consequently, the absorption by biological tissues of such energy will also be relatively high. However, the absorption by water is not as high as the absorption of CO and $CO_2$ laser energy. Thus, the absorption length will be longer for the lasers operating in the 1.4–2.2 micron range. Typically, the absorption length in the body for these latter lasers is about 200 microns. Therefore, it is still possible to operate satisfactorily even with 10–30 microns of blood between the fiber end and the surgical site.

Figure 2:
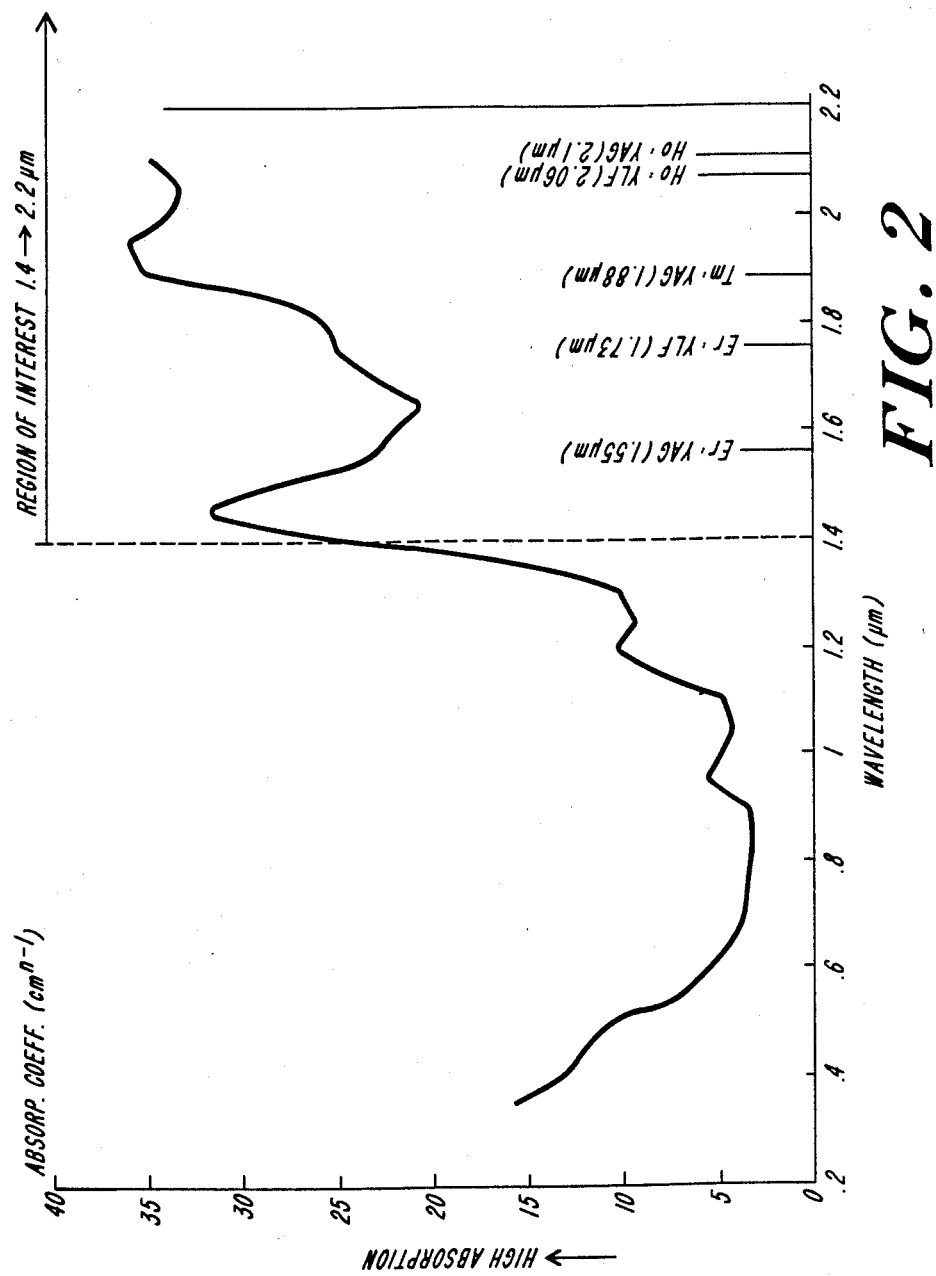
FIG. 2 shows an absorption versus wavelength plot for atherosclerotic plaque obtained in a carotid endarterectomy with the region of interest for the inventive laser sources (1.4–2.2 micrometers) outlined.

Of particular interest is the absorption of the laser energy by atherosclerotic plaque, since an important use of laser catheter systems is angioplasty, particularly the clearing of blocked arteries. FIG. 2 is a plot of the absorption by plaque of electromagnetic energy versus wavelength for energy in the wavelength range of 0.2–2.2 micrometers. As shown in FIG. 2, the absorption by plaque of electromagnetic energy reaches a minimum in the 0.8–1 micrometer wavelength range and generally increases with increasing wavelength in the wavelength region of 1–2.2 micrometers.

In the wavelength range from 1.4–2.2 micrometers, the wavelength range produced by laser in the above-mentioned group, the absorption by plaque is at a relatively high value.

Figure 3:
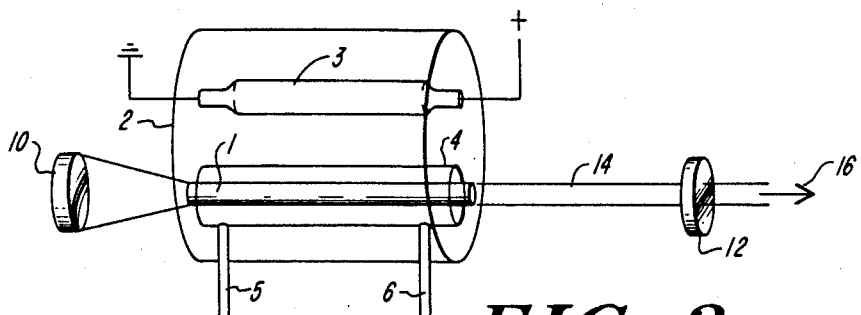
FIG. 3 of the drawing is a schematic diagram of a typical solid state laser construction used in the inventive laser sources.

A schematic diagram of a typical solid-state laser construction is shown in FIG. 3. The laser assembly consists of a laser crystal 1 and an excitation device such as a flashlamp 3. Typically, for the crystal compositions disclosed above, the laser crystal must be cooled to cryogenic temperature to provide low laser-threshhold operation. Cryogenic cooling is typically provided by enclosing crystal 1 in a quartz or fused-silica jacket 4 through which liquid nitrogen is circulated. Liquid nitrogen enters jacket 4 by means of an inlet pipe 5 and leaves by means of an outlet pipe 6. The laser cavity is formed by a high-reflectivity concave mirror 10 and a partial reflector 12.

Generally, the crystal is excited by optical pumping which is, in turn, accomplished by irradiating the crystal with light from a flashlamp 3. A flashlamp which is typically used with the inventive laser compositions is a high-pressure Xenon flashlamp. Lamp 3 may also be surrounded by a quartz flow tube (not shown) through which coolant is pumped.

Crystal 1 and flashlamp 3 are enclosed in a reflector 2 which concentrates the flashlamp energy into the laser crystal. To maximize energy transfer from lamp 3 to crystal 1, the inner surface of reflector 2 is coated with a material chosen to have high-reflectivity at the pumping wavelength of the laser crystal—illustratively, aluminum or silver. In order to provide thermal insulation to prevent condensation on the system optics, it may be necessary to evacuate the interior of reflector 2 or to provide a vacuum jacket around crystal 1.

The construction of cryogenic solid-state lasers is conventional and described in a variety of sources; accordingly such construction will not be discussed further in detail herein. A more complete discussion of construction details of a typical cryogenic laser is set forth in an article entitled "TEM$_{oo}$ Mode Ho:YLF laser", N. P. Barnes, D. J. Gettemy, N. J. Levinos and J. E. Griggs, *Society of Photo-Optical Instrumentation Engineers*, Volume 190—LASL Conference on Optics 1979, pp 297-304.

Figure 4:
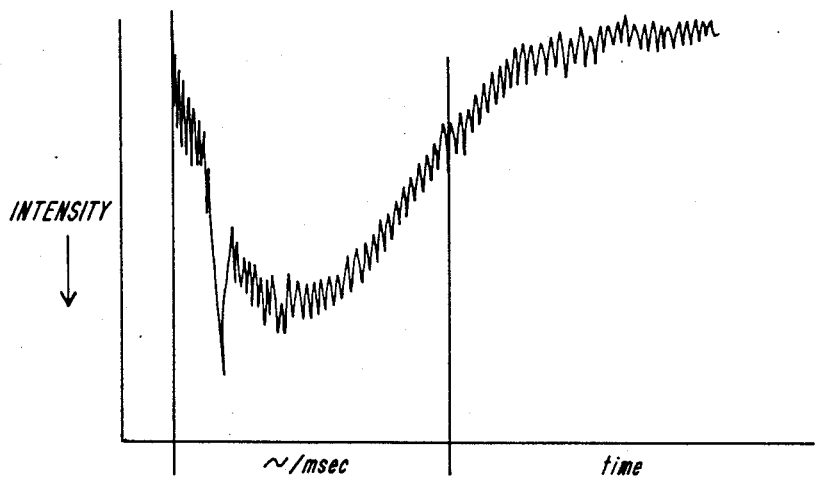
FIG. 4 of the drawing is a plot of laser output intensity versus time for a typical pulse shape developed by a laser shown in FIG. 3 when used for tissue removal.

FIG. 4 of the drawing is a plot of the illustrative pulse shape developed by a laser in the preferred group when used in the "material removal" mode. FIG. 4 shows light intensity along the vertical axis increasing in the downward direction versus time increasing towards the right. Although, as shown in FIG. 4, the laser source has been adjusted to produce an output pulse of relatively long time duration, most of the output energy is released within approximately 1 millisecond of the beginning of the pulse. It should also be noted, as illustrated in FIG. 4, that lasers in the preferred laser group exhibit a "spiking" phenomenon caused by internal relaxation-oscillations in the laser crystal. The spiking behavior causes local increases in laser intensity which have a large magnitude, but a very short time duration. Similar "spiking" behavior has been found advantageous when lasers are used to drill metals and other materials for industrial purposes and it is believed that such "spiking" behavior enhances the laser usefulness for biological material removal.

Figure 5:
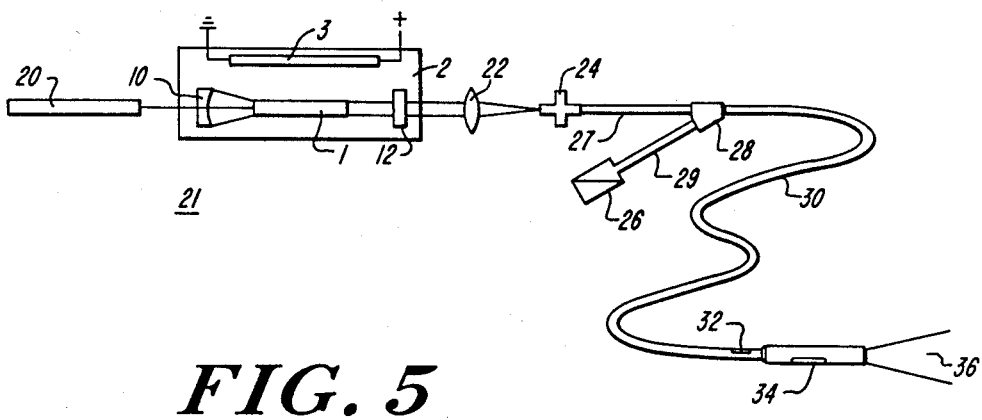
FIG. 5 is a schematic diagram of a laser catheter which employs a single optical fiber for transmitting laser energy to a surgical location.

FIG. 5 is a schematic diagram of a laser/catheter system employing a solid state laser of the type shown in detail in FIG. 3. More specifically, the infrared output energy of laser 21 is focused by a conventional focusing lens onto the end of the optical fiber which is held in a conventional fiber optic connector 24. Fiber optic connector 24 is, in turn, connected to a tube 27 which houses a single optical fiber. Tube 27 is connected to a conventional two-lumen catheter 30 by means of a bifurcation fitting 28.

Illustratively, catheter 30 has two lumens passing axially therethrough to its distal end 34 so that an optical fiber can pass through one lumen and transmit laser energy from fiber optic connector 24 to lens tip 34. As previously mentioned, the optical fiber which passes through the catheter is specially purified to reduce the hydroxyl ion concentration to a low level, thus preventing the laser energy which is transmitted down the fiber from being highly absorbed in the fiber material. A fiber which is suitable for use with the illustrative embodiment is a fused-silica optical fiber part no. 822W manufactured by the Spectran Corporation located in Sturbridge, Mass.

Advantageously, the mirrors and lenses (10, 12 and 22) which are used to form the IR laser cavity and focus the output energy beam are generally only reflective to energy with a wavelength falling within a narrow wavelength band and transparent to energy at other wavelengths. Consequently, the mirrors and lenses are transparent to visible light. An aiming laser 20 (for example, a conventional helium-neon laser) which generates visible light may be placed in series with IR laser 21 to generate a visible light beam. This light beam may be used to align mirrors 10 and 12 and to adjust focussing lens 22 so that the optical fiber system can be aligned prior to performing surgery.

Also, the optical fibers used to transmit the IR energy from laser 21 to the surgical area can also be used to transmit the visible light from the aiming laser 20 to the surgical area. Thus, when the inventive system is used in performing surgery where the surgical area is visible to the surgeon, the light produced by laser 20 passes through the optical fiber in catheter 30 and can be used to aim the probe tip before laser 21 is turned on to perform the actual operation.

The second lumen in catheter 30 is provided for transmission of a flushing fluid or to apply suction to the probe lens tip area to clear the area of blood during surgery. This latter lumen is connected through bifurcation fitting 28 to a second tube 29. Tube 29 may illustratively be terminated by a standard Luer-Lok fitting 26 which allows connection of the catheter to injectors and standard flow fittings. Solutions injected into the catheter through tube 29 pass through the lumen in catheter 30 and exit at the distal end via a small orifice 32.

Probe tip 34 consists of a lens arrangement which forms the laser energy into a beam 36 which is used to perform the surgical operations. An enlarged view of the probe tip is shown in FIGS. 6 and 7.

To ensure that the distal end of optical fiber 18 is spaced and oriented in a precise position with respect to the end of the probe, fiber 18 is mounted in a high-precision holder 58 which has a reduced diameter end 64 that forms a shoulder 68. Shoulder 68, as will hereinafter be described, is used to hold the probe tip assembly together. Holder 58 has a precision-formed axial bore made up of two sections, including a large-diameter section 60 and a narrow-diameter section 63. Holder 58 may be made of glass, ceramic or other material capable of being formed to specified dimensions with precise tolerances.

In order to attach holder 58 to the end of fiber 18, the fiber is first prepared as shown in FIG. 7. More particularly, prior to insertion of fiber 18 into holder 58, a portion of buffer sheath 61 is removed, exposing a length of optically-conductive core 65. Care is taken when stripping buffer sheath 61 from the fiber not to damage the layer of reflective cladding 67 located on the surface of core 65. After stripping, fiber 18 is inserted into holder 58 so that core 65 extends into the small-diameter bore 63 and sheath 61 extends into the large-diameter bore 60. After fiber 18 has been inserted into holder 58, it may be fastened by epoxy cement to permanently affix the components. To complete the assembly, the end of fiber 18 which protrudes beyond surface 62 of holder 58 may be finished flush with the surface by grinding the assembly or by carefully cleaving the fiber.

Referring to FIG. 6, holder 58 (with fiber 18 fastened inside) is mounted within a glass tube 51 to shield the assembly. The front surface, 62, of holder 58 is spaced from the inner surface 142 of planar lens 144, which may be comprised of glass or sapphire, by means of a spacing ring 154. Ring 154 may illustratively be made of radiopaque material so that the catheter tip can be located inside the patient by means of a fluoroscope.

Glass tubing 51 is bent over shoulder 68 of holder 58 to form a constricted end, 65, which holds the probe tip assembly together. A filler, 66, which may be made of a plastic such as TEFLON (trademark of the DuPont corporation for polytetrafluoroethylene) fills the annular space between catheter body 30 and end 65 of glass tube 51. The outer diameter of the entire assembly from catheter body 30 to glass tube 51 is substantially the same, providing a smooth, uniform surface along the entire length of the catheter as indicated in FIG. 6.

Figure 8:
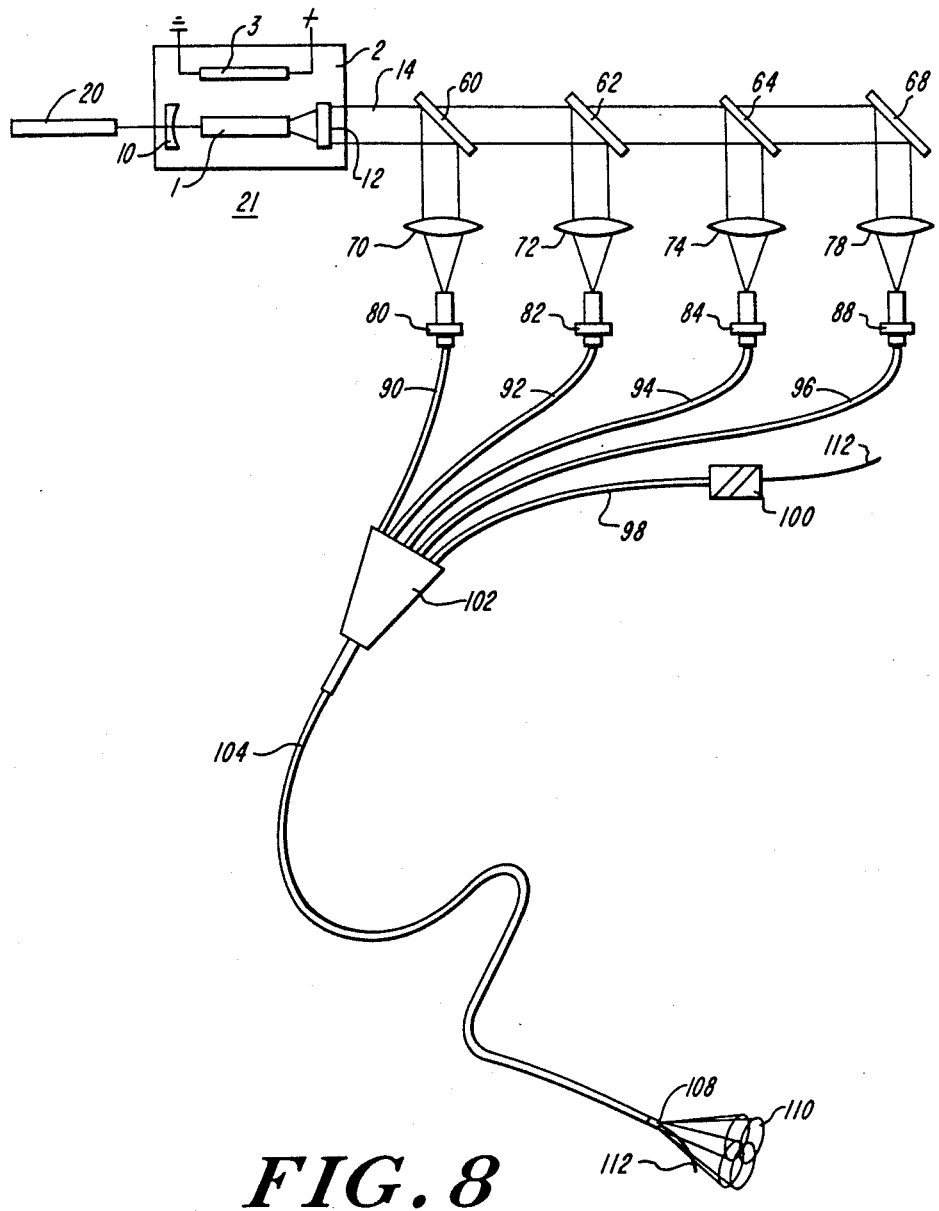
FIG. 8 is a schematic diagram of a wire-guided catheter which employs four optical fibers to increase the area which can be irradiated with the laser light.

FIG. 8 shows a schematic diagram of a wire-guided, four-fiber catheter for use with the present invention. The laser system is set up as previously described with the infrared laser 21 constructed in accordance with the above disclosure. A visible helium-neon aiming laser 20 may also be used in line with laser 21 for aiming purposes as discussed with the single fiber catheter. The output of the infrared laser 21 is directed towards a set of four mirrors 60–68 arranged at a 45° angle with respect to the axis of beam 14.

The first mirror, 60, has a 25% reflective surface and directs approximately ¼ of the energy to focusing lens 70. The second mirror of the set, 62, is a 33% reflector which directs ¼ of the total energy to focusing lens 72. Mirror 64 is a 50% reflector which directs ¼ of the total laser output to focusing lens 74. The last mirror in the set, mirror 68, is a 100% reflector which directs the remaining ¼ of the total energy to focusing lens 78. Mirrors 60–68 and lenses 70–78 are conventional devices.

Focusing lenses 70–78 focus the output energy from IR laser 21 onto four fiber optic connectors, 80–88. Connectors 80–88 are connected, respectively, to tubes 90–96 which are all connected, via a branch connector 102, to catheter 104. Each of tubes 90–96 contains a single optical fiber which transmits ¼ of the total laser output energy through the catheter body to the catheter tip 108. An additional tube 98 is provided which is connected to branch fitting 102 and to a conventional Luer-Lok connector, 100. This latter tube is connected to a central lumen in catheter body 104 through which flushing solutions may be injected or through which a guide wire may be inserted through the catheter for purposes of guiding the catheter to the surgical area.

At catheter tip 108, the four optical fibers which pass through the catheter are arranged symmetrically so that the beams 110 overlap to illuminate a larger area. Tip 108 also has a hole on the center thereof, through which guidewire 112 can protrude to direct the catheter to the proper location.

FIGS. 9 and 10 show detailed views of the illustrative four-fiber catheter tip. The four optical fibers 42 and the inner shaft 40 which holds the fibers, are held in a fiber holder 50 which is preferably formed from a radiopaque material such as stainless steel or platinum. Fiber holder 50 is cylindrical and is provided with a central aperture, 54, which communicates with a lumen 34 of approximately the same size that passes through the center of the catheter body 104. Fiber holder 50 is provided with a plurality of longitudinally extending holes 56 which extend through the wall of holder 50 and receive, in a snug fit, the distal ends of the fiber cores 42. The distal face 58 of the combined fiber cores 42 and holder 50 is polished flat to butt flush against optically transparent cap 52.

Cap 52 is cylindrical and has the same outer diameter as catheter body 104 so that the two pieces define a smooth and continuous diameter. Cap 52 may be formed of a transparent substance such as pyrex glass or sapphire and has an enlarged bore 62 extending in from its proximal end. Bore 62 terminates at its end to form internal shoulder 60. A smaller diameter central aperture, 64, is formed in the distal end of cap 52 which aperture may have the same diameter as aperture 54 in fiber holder 50 and lumen 34 in catheter body 104 to provide a smooth and continuous lumen which opens at the distal tip of the catheter. However, the aperture 64 in tip 52 may also be somewhat narrower than aperture 54 and lumen 34 as long as sufficient clearance is provided to accommodate a guidewire without adversely interfering with fluid flow and pressure measurements.

Cap 52 is secured by an epoxy adhesive (placed on its inner surface 62) to the fiber holder 50 and also to the portion of the inner shaft 40 and fibers 42 which are disposed within the proximal end of the cap 52. The distal end of the catheter body 104 is heat shrunk around the inner shaft 40 and fibers 42 to provide a smooth transition from cap 52 to catheter body 104.

More complete construction details of a four-fiber catheter suitable for use with the illustrative embodiment are given in co-pending U.S. patent application entitled "Wire Guided Laser Catheter", filed on May 22, 1985 by Stephen J. Herman, Laurence A. Roth, Edward L. Sinofsky and Douglas W. Dickinson, Jr.

Figure 11:
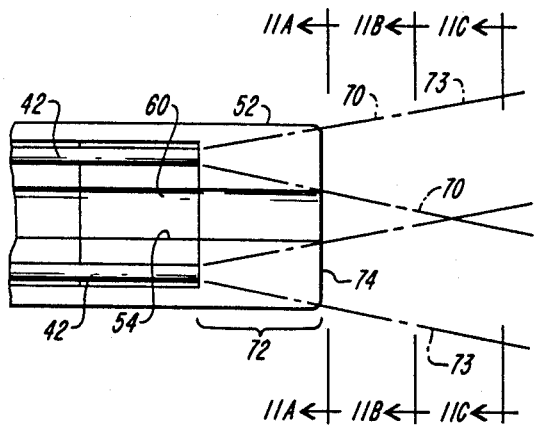
FIG. 11 of the drawing is a schematic diagram of the four fiber catheter emitting a laser beam.

FIG. 11 illustrates the output beam pattern developed by a four-fiber catheter, such as that described above, in which the four fibers are arranged in two diametrically-opposed pairs. The beam pattern from each of the four fiber ends is defined by a cone formed by the ray lines 70 in FIG. 11. The beam from each individual fiber 42 is emitted from the distal face of the fiber 42 and enters the distal segment 72 of ca 52 through the face defining the shoulder 60. The beam from each fiber is divergent and, in the illustrative embodiment, may have a half-angle in the range of 6°–16°, depending on the numerical aperture of the fibers which are used to construct the catheter.

Figure 11A:
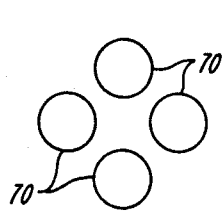
FIG. 11A of the drawing is a schematic diagram of the beam pattern produced by the four-fiber catheter at the location indicated by the line A—A in FIG. 11.
Figure 11B:
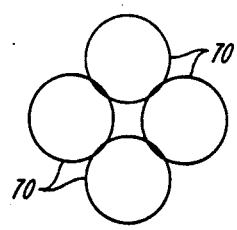
FIG. 11B of the drawing is a schematic diagram of the beam pattern produced by the four fiber catheter at the location indicated by the line B—B in FIG. 11.
Figure 11C:
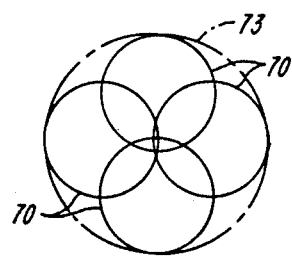
FIG. 11C of the drawing is a schematic diagram of the beam pattern produced by the four fiber catheter at the location indicated by the line C—C in FIG. 11.

The diverging beam from each of the fibers 42 exits from the distal emission face 74 at the end of cap 52. FIGS. 11A, 11B and 11C illustrate the overall beam pattern (in cross-section) which is formed by the output of the four fibers as seen along image planes 11A, 11B and 11C in FIG. 11. At plane 11A, which is located at the emission face 74 of cap 52, the four beams in the illustrative embodiment are still separate. At plane 11B, the diverging beams have spread further and have begun to overlap. At the plane indicated as 11C, the beams have overlapped and define an envelop 73 having an outer diameter which is slightly greater than the outer diameter of the catheter body 104. Preferably, at plane 11C, beams 70 will have overlapped to merge and cover a continuous pattern. Illustratively, such a merger will have occurred within a distance from the distal face 74 of tip 52 which is approximately equal to the outer diameter of catheter 104 (a typical diameter is 1.5 millimeters).

What is claimed is:

1. A system for the percutaneous removal of atherosclerotic plaque comprising:
    a laser energy source including means for operating said laser energy source in a pulsed mode with an output wavelength in the range of about 1.4–2.2 micrometers, and for operating said laser energy source at an energy level sufficient to remove atherosclerotic plaque;
    an optical fiber for conducting laser energy from said laser energy source from a proximal end of said fiber to a surgical site at a distal end of said optical fiber; and
    means for directing the output of said laser energy source to the proximal end of said optical fiber.

2. A system for the removal of atherosclerotic plaque in accordance with claim 1 wherein said laser energy source includes means for operating said laser source with a pulse width of the order of 1 millisecond.

3. A system for the removal of atherosclerotic plaque in accordance with claim 1 wherein said laser energy source includes means for operating said laser source at a repetition rate in the range of from about 1 to about 10 pulses per second.

4. A system for the removal of atherosclerotic plaque in accordance with claim 1 wherein said optical fiber comprises a silica fiber purified to reduce the hydroxyl ion content as low as possible.

5. A method for the percutaneous removal of atherosclerotic plaque comprising the steps of:
    percutaneously inserting a catheter containing an optical fiber into the body;
    guiding a distal end of the optical fiber to a surgical site within the body;
    operating a laser energy source in a pulsed mode with an output beam having a wavelength in the range of from about 1.4 to about 2.2 micrometers, an energy level of at least about 0.57 joules per square millimeter per pulse, and a repetition rate in the range of from about 1 to about 10 pulses per second;
    directing the output of the laser energy source to a proximal end of the optical fiber; and
    directing laser energy propagating down the optical fiber to the surgical site at the distal end of the optical fiber.

6. A system for the removal of atherosclerotic plaque comprising:
    a laser energy source including means for operating said laser energy source in a pulsed mode with an output wavelength in the range of from about 1.4–2.2 micrometers, and for operating said laser energy source at an energy level of at least about 0.57 joules per square millimeter per pulse;
    an optical fiber for conducting laser energy from said laser energy source from a proximal end of said fiber to a surgical site at a distal end of said optical fiber; and
    means for directing the output of said laser energy source to the proximal end of said optical fiber.

7. A system for the removal of atherosclerotic plaque in accordance with claim 6 wherein said laser energy source includes means for operating said laser source with a pulse width of the order of 1 millisecond.

8. A system for the removal of atherosclerotic plaque in accordance with claim 6 wherein said laser energy source includes means for operating said laser source at a repetition rate in the range of from about 1 to about 10 pulses per second.

9. A system for the removal of atherosclerotic plaque in accordance with claim 6 wherein said optical fiber comprises a silica fiber purified to reduce the hydroxyl ion content as low as possible.

10. A method for the percutaneous removal of atherosclerotic plaque comprising the steps of:
    percutaneously inserting a catheter containing an optical fiber into the body;
    guiding a distal end of the optical fiber to a surgical site within the body;
    operating a laser energy source in a pulsed mode with an output beam having a wavelength in the range of from about 1.4 to about 2.2 micrometers and an energy level of at least about 0.57 joules per square millimeter per pulse;
    directing the output of the laser energy source to a proximal end of the optical fiber; and
    directing laser energy propagating down the optical fiber to the surgical site at the distal end of the optical fiber.

11. A method for the percutaneous removal of atherosclerotic plaque in accordance with claim 10 wherein said operating step comprises the step of operating the laser energy source with a pulse width of the order 1 millisecond.

12. A method for the percutaneous removal of atherosclerotic plaque in accordance with claim 10 wherein said operating step comprises the step of operating the laser energy source at a repetition rate in the range of from about 1 to about 10 pulses per second.

13. A method for the percutaneous removal of atherosclerotic plaque in accordance with claim 10 wherein said operating step comprises the step of operating the laser energy source at an output wavelength of about 2.06–2.10 micrometers.

14. A method for the percutaneous removal of atherosclerotic plaque in accordance with claim 10 further comprising the step of reducing the hydroxyl ion content of the optical fiber to be as low as possible.

15. A system for the removal of atherosclerotic plaque comprising:
    a laser energy source including means for operating said laser energy source in a pulsed mode with an output wavelength in the range of 1.4–2.2 micrometers, and for operating said laser energy source at an energy level of at least about 1 joule per pulse for a surgical site or the order of 1.5 millimeters in diameter;
    an optical fiber for conducting laser energy from said laser energy source from a proximal end of said fiber to a surgical site at a distal end of said optical fiber; and means for directing an output of said laser source to the proximal end of said optical fiber.

16. A system in accordance with claim 15 wherein said optical fiber comprises a silica fiber purified to reduce the hydroxyl ion content as low as possible.

17. A system in accordance with claim 15 wherein said laser source comprises a Holmium-doped Yttrium-Aluminum-Garnet laser.

18. A system in accordance with claim 15 wherein said laser source comprises an Erbium-doped Yttrium-Aluminum-Garnet laser.

19. A system in accordance with claim 15 wherein said laser source comprises a Holmium-doped Yttrium-Lithium-Fluoride laser.

20. A system in accordance with claim 15 wherein said laser source comprises an Erbium-doped Yttrium-Lithium-Fluoride laser.

21. A system in accordance with claim 15 wherein said laser source comprises a Thulium-doped Yttrium-Aluminum-Garnet laser.

22. A system for the removal of biological tissue in accordance with claim 15 further comprising an aiming laser source means for generating visible light output and means for directing said visible light output through said laser source and said optical fiber to align said laser and said fiber and to visually illuminate said surgical site.

23. A system in accordance with claim 15 wherein said laser source includes means for operating said laser source with a pulse width of the order of 1 millisecond.

24. A system in accordance with claim 15 wherein said laser energy source includes means for operating said laser source at a repetition rate in the range of from about 1 to about 10 pulses per second.

25. A system in accordance with claim 15 wherein the surgical site is accessible percutaneously, said system further comprising means for percutaneously placing the distal end of said optical fiber.

26. A system for the removal of atherosclerotic plaque comprising:
   a laser energy source including means for operating said laser energy source in a pulsed mode with an output wavelength in the range of 1.4–2.2 micrometers, and for operating said laser energy source operating at an energy level of at least about 1 joule per pulse for a surgical site of the order of 1.5 millimeters in diameter;
   a catheter having at least one lumen passing therethrough;
   at least one optical fiber comprised of silica passing through said catheter lumen, said silica fiber being purified to reduce the hydroxyl ion content as low as possible;
   a focusing lens means for directing the output of said laser source onto the proximal end of said optical fiber; and
   a lens attached to the distal end of the optical fiber for directing laser energy propagating down said fiber to a surgical site.

27. A system in accordance with claim 26 further comprising a fiber optic connector affixed to the proximal end of said fiber for holding said fiber.

28. A system in accordance with claim 26 wherein said catheter has an additional lumen passing therethrough, said additional lumen having an opening at the proximal and distal ends for communicating with said surgical site.

29. A system in accordance with claim 26 wherein said laser source comprises a Holmium-doped Yttrium-Aluminum-Garnet laser.

30. A system in accordance with claim 26 wherein said laser source comprises an Erbium-doped Yttrium-Aluminum-Garnet laser.

31. A system in accordance with claim 26 wherein said laser source comprises a Holmium-doped Yttrium-Lithium-Fluoride laser.

32. A system in accordance with claim 26 wherein said laser source comprises an Erbium-doped Yttrium-Lithium-Fluoride laser.

33. A system in accordance with claim 26 wherein said laser source comprises a Thulium-doped Yttrium-Aluminum-Garnet laser.

34. A system in accordance with claim 26 wherein said laser source includes means for operating said laser source with a pulse width of the order of 1 millisecond.

35. A system in accordance with claim 26 wherein said laser energy source includes means for operating said laser source at a repetition rate in the range of from about 1 to about 10 pulses per second.

36. A system in accordance with claim 26 further comprising an aiming laser source means for generating visible light output and means for directing said visible light output through said laser source and said optical fiber to align said laser and said fiber and to visually illuminate said surgical site.

37. A system in accordance with claim 26 wherein the surgical site is accessible percutaneously, said system further comprising means for percutaneously placing the distal end of said optical fiber.

38. A system for the removal of atherosclerotic plaque comprising:
   a Holmium-doped laser energy source including means for operating said laser energy source in a pulsed mode with an output wavelength in the range of from about 2.06–2.1 micrometers, and for operating said laser energy source at an energy level of at least about 1 joule per pulse for a surgical site of the order of 1.5 millimeters in diameter;
   an optical fiber for conducting laser energy from said laser energy source from a proximal end of said fiber to a surgical site at a distal end of said optical fiber; and
   means for directing an output of said laser source to the proximal end of said optical fiber.

39. A system in accordance with claim 38 wherein said laser includes means for operating said laser source with a pulse width of the order of 1 millisecond.

40. A system in accordance with claim 38 wherein said laser energy source includes means for operating said laser source at a repetition rate in the range of from about 1 to about 10 pulses per second.

41. A system in accordance with claim 38 wherein the surgical site is accessible percutaneously, said system further comprising means for percutaneously placing the distal end of said optical fiber.

* * * * *